United States Patent [19]

Scaccia

[11] Patent Number: 4,832,878

[45] Date of Patent: May 23, 1989

[54] GAS-LIQUID PROCESS FOR PREPARING ISOBUTYRYL FLUORIDE AND REACTOR THEREFOR

[75] Inventor: Carlo Scaccia, Worthington, Ohio

[73] Assignee: Ashland Oil, Inc., Ashland, Ky.

[21] Appl. No.: 811,150

[22] Filed: Dec. 19, 1985

Related U.S. Application Data

[63] Continuation of Ser. No. 621,780, Jun. 18, 1984, abandoned.

[51] Int. Cl.$^4$ .............................................. C07C 51/14
[52] U.S. Cl. .............................. 260/544 A; 260/544 F
[58] Field of Search ................... 260/544 A; 422/234; 562/521

[56] References Cited

U.S. PATENT DOCUMENTS 4,303,594 12/1981 Norton et al. ................... 260/544 A
4,452,999 6/1984 Besecke et al. ...................... 562/521

OTHER PUBLICATIONS

Perry, Robert H. et al., *Chemical Engineers' Handbook*, 5th Ed. (1979), McGraw-Hill, Publ. at pp. 4-20 and 4-21.

*Primary Examiner*—Paul J. Killos
*Attorney, Agent, or Firm*—John F. Jones

[57] ABSTRACT

A process and apparatus using two gas liquid separations when carbonylating propylene to isobutyryl fluoride in hydrogen fluoride result in a savings in recycle pumping energy compared to a one gas-liquid separation process.

4 Claims, 1 Drawing Sheet

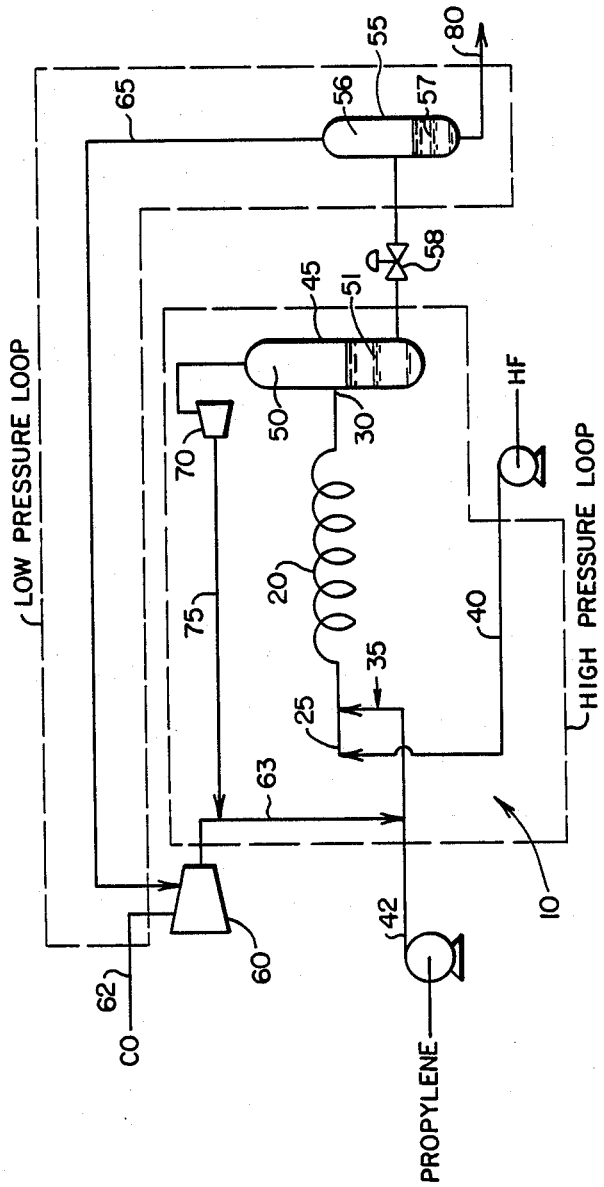

GAS-LIQUID PROCESS FOR PREPARING ISOBUTYRYL FLUORIDE AND REACTOR THEREFOR

CROSS REFERENCE TO RELATED APPLICATIONS

This application is a continuation of the pending application Ser. No. 06/621,780 filed June 18, 1984.

BACKGROUND OF THE INVENTION a. Field of the Invention

The invention pertains to a process for preparing isobutyryl fluoride from carbon monoxide, propylene and hydrogen fluoride.

b. Description of the Prior Art

U.S. Pat. No. 2,831,877 describes a batch process for making carboxylic acids from olefins, carbon monoxide, an acidic medium such as hydrogen fluoride and water. However, the process is uneconomical because high polymeric acids and other compounds form, causing poor yields of carboxylic acids. U.S. Pat. No. 3,059,007 describes an improved process in which the mono-olefinic charge is hydrogenated prior to reaction to remove any polyolefinic materials which cause polymerization, but the resulting yields of mono-carboxylic acids are only 53.6 to 62 percent. European Patent Application No. 0-017-441 describes reacting a boron trifluoride catalyst and an alcohol in equal molar quantities, followed by separating the ester formed and the catalyst. This process cannot be used to form the isobutyryl fluoride. European Pat. No. 0,031,886 describes a process for making isobutyric acid or its lower alkyl esters, but such a process cannot be used to make isobutyryl fluoride. Belgium Patent No. 893,419 describes a slow semi-batch process for producing isobutyryl fluoride which decreases polymerization; however, the process is not suitable for a fast, commercially continuous process. Belgium Pat. No. 893,415 describes a fast, continuous, high pressure liquid process to form isobutyryl fluoride, but the high pressure equipment for the rapid flow rates is expensive. However, none of the above-mentioned prior art teach or suggest how to reduce the expensive costs of recovering and recycling carbon monoxide.

The present invention overcomes the expensive recovery and recycling of carbon monoxide of the prior art for a complex co-current gas-liquid reaction.

SUMMARY OF THE INVENTION

The invention provides a continuous co-current pressurized gas-liquid process and the apparatus therefor for producing isobutyryl fluoride from carbon monoxide, hydrogen fluoride and propylene. The process comprises: Step(a), a first fluid mixture comprised of carbon monoxide and propylene is co-currently reacted under pressure in a reactor with a first liquid comprised of hydrogen fluoride at conditions whereby isobutyryl fluoride forms; Step(b) the product mixture from Step(a) is separated at a pressure substantially equal to the reaction pressure into a second gas mixture comprised of carbon monoxide and a second liquid comprises of isobutyryl fluoride, hydrogen fluoride and carbon monoxide; Step(c), the second liquid from Step(b) is separated at a pressure substantially below the reaction pressure into a third gas mixture comprises of carbon monoxide and a third liquid comprised of isobutyryl fluoride, and hydrogen fluoride. Step(d), the second and third gas mixtures from Steps(b) and (c) together with make-up carbon monoxide and propylene, are formed into the first fluid mixture. Step(e), the first fluid mixture from Step(d) is recycled to react as in Step(a) so that isobutyryl fluoride is continuously formed. In another embodiment, the hydrogen fluoride is separated and recycled.

BRIEF DESCRIPTION OF THE DRAWING

The drawing shows a schematic representation of the process and reactor.

DESCRIPTION OF THE INVENTION (a) General Description

The invention concerns a continuous gas-liquid pressurized process for producing isobutyryl fluoride from carbon monoxide, propylene and hydrogen fluoride whereby the carbon monoxide or both carbon monoxide and hydrogen fluoride are inexpensively recycled so that waste carbon monoxide or waste hydrogen fluoride and carbon monoxide is kept to a minimum.

The process is based on the following steps:

Step(a) co-currently reacting under pressure in a co-current reactor a first fluid mixture comprised of carbon monoxide and propylene with a first liquid comprised of hydrogen fluoride under conditions whereby isobutyryl fluoride forms;

Step(b) separating at a pressure substantially equal to the reaction pressure the product mixture formed in Step(a) into a second gas mixture comprised of carbon monoxide, and into a second liquid comprised of isobutyryl fluoride, hydrogen fluoride, and carbon monoxide;

Step(c) separating at a pressure substantially below the reaction pressure, the second liquid from Step(b) into a third gas mixture substantially comprised of carbon monoxide and a third liquid comprised of isobutyryl fluoride and hydrogen fluoride;

Step (d) forming the first fluid mixture from the second and third gas mixtures of Steps(b) and (c) together with make-up carbon monoxide and propylene;

Step(e) recycling the first fluid mixture from Step(d) to the reactor for reaction as in Step(a) whereby isobutyryl fluoride forms in a continuous process.

The first liquid is comprised of hydrogen fluoride, preferably of anhydrous hydrogen fluoride, and may include a small amount of isobutyryl fluoride, carbon monoxide, and other inerts such as carbon dioxide, nitrogen and alkanes which do not effect the reaction.

The first fluid mixture is comprised of carbon monoxide and propylene, but can also include other inerts such as alkanes like propane and/or carbon dioxide and/or nitrogen.

In another embodiment of the reaction, the hydrogen fluoride is separated from the third liquid formed from the second gas-liquid separation of Step(c). The separation can easily be done by simple distillation. The separated hydrogen fluoride is also recycled to react as in Step(a).

(b) General Description of the Apparatus

The apparatus (also called the reactor) (1)) for conducting a continuous co-current gas-liquid process under pressure to form isobutyryl fluoride from a liquid comprised of hydrogen fluoride and a fluid mixture comprised of carbon monoxide and propylene is schematically shown in the attached drawing. The apparatus comprises at least one reactor tube (20) having a back end (30) and a front end(25). The front end (25) has connected to it a means (35) for injecting a fluid mixture, such as propylene and carbon monoxide into a liquid, so that the gas-liquid reaction mixture enters the reactor tube (20) for reaction. The means (35) for injection of a fluid mixture can be an aspirator nozzle, a jet nozzle, or other suitable devices known in the art.

A means (40) for introducing liquid comprised of hydrogen fluoride under pressure connects to the front end (25) of the reactor tube (20). One such means comprises a liquid pump as shown in the drawing connected by a line to the front end (25) of the reactor tube (20). Other suitable devices known in the art may also be used.

A first gas-liquid separator (45) (which has means for refrigeration) with a liquid section (51) and a gas section (50) connects to the back end (30) of the reactor tube (20).

A means (42) for introducing propylene as a liquid, or gas, or fluid into the reactor (10) is connected to the means (35) for injecting a fluid mixture into the liquid stream. The means (42) for introducing propylene as shown comprises a constant flow-liquid pump and line which connects to the fluid injecting means (35). Other suitable devices known in the art may also be used for introducing propylene into the reactor.

A second gas-liquid separator (55) which has a gas section (56) and a liquid section 957) connects to at least one reducing valve (58). The reducing valve (58) connects to the liquid section (51) of the first gas-liquid separator (45) and to the gas section (56) of the second gas-liquid separator (55).

A first compressor pump (60) preferably a staged compressor pump, is used to compress the gas mixture comprises mainly of carbon monoxide coming from the gas section (56) of the second gas-liquid separator through second line (65).

The first compressor pump (60) is connected to carbon monoxide source (62); for example, a carbon monoxide source from a refinery. The first compressor pump (60) compresses the carbon monoxide from source (62) and the gas mixture from the second gas-liquid separator (55) to a pressure above the pressure within the reactor tube (20) so that the gases from the first compressor pump (60) enter the reactor tube (20) for reaction as described herein.

A first line (63) connects to the outlet of the first compressor pump (60) and to the means (42) for introducing a fluid comprised of propylene into the mixture whereby the gas exiting the first compressor pump (60) is transferred into the fluid comprised of propylene which is introduced into the reaction tube (20).

A second line (65) connects to the gas section (56) of the second gas-liquid separator (55) and to the first compressor pump (60) whereby the gas from within the second gas-liquid separator (55) transfers to the first compressor pump (60).

A second compressor pump (70) connects to the gas section (50) of the first gas-liquid separator and to first line (63) which connects to the outlet of the first compressor pump (60). The second compressor pump (70) boosts the pressure of the gas exiting the first gas-liquid separator (45) to that above the pressure within the first line (63) whereby the gas from the first gas-liquid separator (45) is recycled into the reactor tube (20).

A third line (75) connects to the first line (63) and to the outlet of the second compressor pump (70) whereby the gas from the second compressor pump is transferred into the gas from the first compressor (60).

A means (80) for removing the second liquid from the second gas-liquid separator (55) is connected to the liquid section (57) whereby the second liquid which comprises liquid hydrogen fluoride and isobutyryl fluoride is removed from the apparatus (reactor) (10). The second liquid can be transferred to a suitable storage tank or conveyor tank for further processing. Preferably, the second liquid is transferred to a separation means (not shown) such as a distillation unit whereby the isobutyryl fluoride and hydrogen fluoride are separated and the hydrogen fluoride is liquified and transferred to the means (40) for introducing liquid hydrogen fluoride under pressure for recycling.

EXAMPLES

The following examples will illustrate the process and apparatus of the invention.

Procedure

In the examples, which follow and use the process and apparatus described herein, carbon monoxide from the source (62) flows through the first compressor pump (60) into first line (63) where it is mixed with the gas mixture comprised of CO coming through third-line (75) from the second compressor pump (70). The gas mixture exiting first line (63) mixes with a fluid comprised of propylene from the means (42) for introducing propylene, to form a first fluid mixture which enters the front end (25) of the reactor tube (20) through ejection means (35) and mixes with the liquid hydrogen fluoride flowing into front end (25) of the reactor tube (20) through the means (40) for introducing liquid hydrogen fluoride into the reactor tube (20). The reaction mixture of gas-liquid co-currently reacts in reactor tube (20) to form isobutyryl fluoride and the product mixture comprised for example of unreacted propylene, carbon monoxide, hydrogen fluoride and isobutyryl fluoride and possible inerts passes into the first gas liquid separator (45). The gas from the first liquid separator (45) passes through the second compressor pump (70) where it is compressed and passed into first line (63) as mentioned above.

The first liquid which has dissolved CO therein from the liquid section (51) of the first gas-liquid separator (45) (which has means for refrigeration) passes through the reducing valve (58) and into the second gas-liquid separator (55). The gas from the gas section (56) of the second gas-liquid separator (55) passes through the second line (65) into the first compressor pump (60) where it, together with make-up carbon monoxide from a source 962) is recycled for further reaction in reactor tube (20) as described herein.

EXAMPLE I

This example followed the procedure described above and the reaction is conducted at five hundred and fifty (550) pounds per square inch absolute (psia) (37.9 bars), 113° F. (45° C.), at a propylene flow rate of 24,841 lbs/hour (11,278. kg/hour), a carbon monoxide flow rate of 115,800 lbs/hour (52,573 kg/hour), and a hydrogen fluoride flow rate of 165,400 lbs/hour (75,092 kg/hour).

The first compressor (60) is sized for a delta ($\Delta$) pressure of 550–15 psi at an efficiency of 70%. The second compressor (70) is sized by the high pressure transfer (loop) with delta (Δ) pressure of (550–500) psi (3.45 bars), at an efficiency of 70%.

The amount of Horse Power (HP) and refrigeration requirements (duty) as millions BTU per hour are shown in Table I.

EXAMPLE II

The example is similar to Example I except that the first compressor (60) is sized for a delta (Δ) pressure of 2500–15 psi with an efficiency of 70%. The high pressure loop for the second compressor (70) is sized for a pressure differential (Δp) of (2500–2400) psi (6.90 bars). The pressure of the reaction is 2500 psia (172 bars). The amount of horse power (H.P.), and refrigeration requirements (duty) as million of BTU's per hour are shown in Table I.

COMPARATIVE EXAMPLES

The following comparative examples III and IV show the horsepower and refrigeration duty of the process based on the same flow rates, reactor pressure and reaction conditions as in Examples I and II.

In these comparative examples, the apparatus used does not have a second compressor (70), third line (75), or a first gas liquid separator (45). Instead, the product mixture from the reactor tube (20) passes through reducing valve (58) into the second gas-liquid separator (55).

COMPARATIVE EXAMPLE III

The example is based at the same conditions as Example I, except that only one compressor (60) is used. The amounts of Horse Power (H.P.) and refrigeration duty (Million BTU/hr), are shown in Table I.

COMPARATIVE EXAMPLE IV

The example is run as in Example II, except that one compressor (60) is used. The amounts of HP and refrigeration duty as (Millions of BTU's/ hr) are shown in the Table I.

TABLE I

| Example | Compressor (60) HP | Compressor (70) HP | Increase In Refrigeration Duty from the 2 Compressors Case HP | Compressors HP |
|---|---|---|---|---|
| I. Two Compressors Reactor Pressure: 550 Psia | 1858 | 158 | — | 2016 |
| II. Two Compressors. Reactor Pressure: 2500 psia | 4821 | 45 | — | 4866 |
| III. One Compressor. Reactor Pressure: 550 psia | 6299 | — | 938 | 7237 |

TABLE I-continued

| Example | Compressor (60) HP | Compressor (70) HP | Increase In Refrigeration Duty from the 2 Compressors Case HP | Compressors HP |
|---|---|---|---|---|
| IV. One Compressor. Reactor Pressure: 2500 psia | 10,212 | — | 684 | 10,896 |

The equation used to calculate the isentropic multistage compression horsepower requirements, assuming equal division of work between cylinders and intercooling of gas to original intake temperature, is taken from *Plant Design and Economics for Chemical Engineers*, Peters, Max S. and Timmerhaus, Klaus D., McGraw Hill, New York, 2nd Ed., 1968, page 463–464, which reference is incorporated herein by reference thereto. The values requires for the use of the equation are presented in Table 2.

TABLE 2

| Example | k | $N_s$ | $P_1$ | $P_2$ | qfm | HP @ .7 Efficiency |
|---|---|---|---|---|---|---|
| I, 2 Compressor 550 psia | 1.55 | 3 | 60 | 550 | 1331 | 1261 |
|  | 1.72 | 1 | 500 | 550 | 522 | 158 |
| II, 2 Compressor 2500 psia | 1.52 | 5 | 60 | 2500 | 2658 | 4224 |
|  | 1.48 | 1 | 2400 | 2500 | 73 | 45 |
| III, 1 Compressor 550 psia | 1.74 | 3 | 60 | 550 | 5857 | 5702 |
| IV, 1 Compressor 2500 psia | 1.74 | 5 | 60 | 2500 | 5857 | 9615 |
| CO Pre-pressurization (adds to all above) | 1.40 | 2 | 15 | 60 | 4161 | 597 |

The refrigeration duty for the examples are shown in Table 3.

TABLE 3*

| | DUTY MM BTU/HR | | | |
|---|---|---|---|---|
| | Example I | Example II | Example III | Example IV |
| Refrigeration −30° to 100° F. | .7 | 2.4 | 6.95 | 6.95 |
| Δ Cooling duty wrt*** two compressor cases | — | — | 6.25 | 4.55 |
| Δ HP Required using R-11** refrigerant wrt two compressor case | — | — | 938 | 684 |

*Chemical Engineering Handbook, Fifth Edition, Section 12, pgs. 29–49. Incorporated herein by reference thereto.
**Trichlorofluoromethane
***With respect to The summary of HP requirements for the examples are shown in Table 4.

TABLE 4

| Example | CO Pre-Pressurization.HP (Unit 60) | High Pressure Recycle.HP (Unit 70) | Low Pressure Recycle.HP (Unit 60) | Increased Refrigerant Duty.HP | Total Recycle HP |
|---|---|---|---|---|---|
| I, 2 Compressor 550 psia | 597 | 158 | 1,261 | — | 2,016 |
| II, 2 Com- | 597 | 45 | 4,224 | — | 4,866 |

TABLE 4-continued

| Example | | CO Pre-Pressurization.HP (Unit 60) | High Pressure Recycle.HP (Unit 70) | Low Pressure Recycle.HP (Unit 60) | Increased Refrigerant Duty.HP | Total Recycle HP |
|---|---|---|---|---|---|---|
| | pressor 2500 psia | | | | | |
| III, | 1 Compressor 550 psia | 597 | — | 5,702 | 938 | 7,237 |
| IV, | 1 Compressor 2500 psia | 597 | — | 9,615 | 684 | 10,896 |

In the high pressure case (2500 psia), the amount of CO dissolved in the liquid phase is 5.5 times greater than in the 550 psia case; therefore, substantially less gas/vapor is available at the 2400 psia phase separator to recycle in an elevated pressure loop. The magnitude of HP saved with the two-compressor design is greater at 2500 psia than at 550 psia, even though the fraction recycled at higher pressure is much smaller.

From the above examples it is readily seen that the process and apparatus described herein and in the claims results in a large savings of cost and energy requirements; for example, a saving of 5,221 H.P. at 550 psia, and 6,030 H.P. at 2,500 psia.

Although the invention has been described with reference to specific details of certain illustrative embodiments, it is not intended that it shall be limited thereby except insofar as such details appear in the accompanying claims.

I claim:

1. A continuous co-current gas-liquid process for producing isobutyryl fluoride by carbonylation of propylene with carbon monoxide and hydrogen fluoride, which comprises:
   (a) co-currently reacting under a pressure of from about 550 to about 2500 psia in a co-current reactor a first fluid stream comprised of carbon monoxide and propylene with a first liquid comprised of hydrogen fluoride whereby isobutyryl fluoride forms;
   (b) separating at a pressure which is substantially equal to the reaction pressure, the product mixture formed in Step(a) into a second gas mixture comprised of carbon monoxide, and a second liquid comprised of isobutyryl fluoride, hydrogen fluoride, and carbon monoxide;
   (c) separating at a pressure substantially below the reaction pressure, the second liquid from Step(b) into a third gas mixture comprised of carbon monoxide and a third liquid comprised of isobutyryl fluoride and hydrogen fluoride;
   (d) forming the first fluid mixture comprised of carbon monoxide and propylene from the second and third gas mixtures from Steps(b) and (c) and make-up carbon monoxide and propylene, and
   (e) recycling the first fluid mixture of Step(d) to react as in Step(a) whereby isobutyryl fluoride forms in a continuous process.

2. A continuous co-current gas-liquid process for producing isobutyryl fluoride by carbonylation of propylene with carbon monoxide in hydrogen fluoride which comprises:
   (a) co-currently reacting at a pressure of from about 550 to about 2500 Psia in a co-current reactor a first fluid mixture stream comprised of carbon monoxide and propylene with a first liquid stream comprised of hydrogen fluoride under conditions whereby isobutyryl fluoride forms;
   (b) separating at a pressure which is substantially equal to the reaction pressure the product mixture formed in Step(a) into a second gas mixture comprised of carbon monoxide and a second liquid comprised of isobutyryl fluoride, hydrogen fluoride and carbon monoxide;
   (c) separating at a pressure substantially below the reaction pressure the second liquid from Step(b) into a third gas mixture comprised of carbon monoxide and a third liquid comprised of isobutyryl fluoride and hydrogen fluoride;
   (d) forming the first fluid mixture comprised of carbon monoxide and propylene from the second and third gas mixture from Step(b) and (c) and make-up carbon monoxide and propylene;
   (e) separating the hydrogen fluoride from the third liquid of Step(c), and
   (f) recycling the hydrogen fluoride from Step(e) and the first fluid mixture from Step(d) to the reactor for reaction as in Step(a), so as to continuously form isobutyryl fluoride.

3. The process as defined in claim 1 wherein the step (b) separation pressure is from about ninety (90) to ninety-six (96) percent of the reaction pressure of step (a), and the step (c) separation pressure is from about two (2) to about eleven (11) percent of the reaction pressure of step (a).

4. The process as defined in claim 2 wherein the step (b) separation pressure is from about ninety (90) to ninetysix (96) percent of the reaction pressure of step (a) and the step (c) separation pressure is from about two (2) to about eleven (11) percent of the reaction pressure of step (9).

* * * * *